United States Patent [19]

Fenoglio

[11] 4,002,644
[45] Jan. 11, 1977

[54] BIS-(1,4-DIHYDRONAPHTHO)[2,3-C; 2,3-F]1,2,5-TRITHIEPANE

[75] Inventor: David J. Fenoglio, Carol Stream, Ill.

[73] Assignee: Standard Oil Company a corporation of Indiana, Chicago, Ill.

[22] Filed: May 19, 1975

[21] Appl. No.: 578,620

Related U.S. Application Data

[62] Division of Ser. No. 432,996, Jan. 14, 1975, Pat. No. 3,923,753.

[52] U.S. Cl. .......................................... 260/327 B
[51] Int. Cl.$^2$ ...................................... C07D 341/00
[58] Field of Search ................... 260/327 R, 327 B

[56] References Cited

UNITED STATES PATENTS 3,923,753  12/1975  Fenoglio ...................... 260/327 B

*Primary Examiner*—Henry R. Jiles
*Assistant Examiner*—C. M. S. Jaisle
*Attorney, Agent, or Firm*—William H. Magidson; Arthur G. Gilkes; William T. McClain

[57] ABSTRACT

2,3-thioepoxytetralin, poly(2,3-thioepoxytetralin) and bis-(1,4-dihydronaphtho)[2,3-c; 2,5-f]1,2,5-trithiepane.

1 Claim, No Drawings

BIS-(1,4-DIHYDRONAPHTHO)[2,3-C; 2,3-F]1,2,5-TRITHIEPANE

This is a division, of application Ser. No. 432,996, filed Jan. 14, 1975 now U.S. Pat. No. 3,923,753, issued Dec. 2, 1975.

This invention relates to 2,3-thioepoxytetralin and derivative thereof.

In commonly assigned U.S. Pat. No. 3,699,020, there is disclosed an efficient electrochemical method of producing 1,4-dihydronaphthalene. The general object of this invention is to provide useful new compounds and polymers based on 1,4-dihydronaphthalene. A more specific object of this invention is to provide useful sulfur compounds and polymers based on 1,4-dihydronaphthalene. Other objects appear hereinafter.

In one aspect this invention is directed to 2,3-thioepoxytetralin.

In a second aspect this invention is directed to poly(2,3-thioepoxytetralin).

In a third aspect this invention is directed to Bis-(1,4-dihydronaphtho) [2,3-c; 2,3-f] 1,2,5-trithiepane.

I have now found that epoxidized 1,4-dihydronaphthalene can be converted into 2,3-thioepoxytetralin. Biological testing has shown that this compound exhibited necrosis to fall pancium, jimsonweed and moderate retardation to pigweed and wild morningglory weed. The 2,3-thioepoxytetralin can be polymerized to form poly(2,3-thioepoxytetralin) which can be used as fibers, adhesives, surface active agents, etc. or converted to Bis-(1,4-dihydronaphtho) [2,3-c; 2,3-f] 1,2,5-trithiepane. The latter compound can be used to control mexican bean beetle.

Briefly, 2,3-thioepoxytetralin can be prepared by reacting 2,3-epoxytetralin with a thiocyanate.

In somewhat greater detail, 2,3-thioepoxytetralin can be prepared by reacting 2,3-epoxytetralin with a thiocyanate, such as sodium or potassium thiocyanate, in an aqueous alcoholic medium under ambient conditions. Any water miscible alcohol can be used, such as methanol, ethanol, isopropanol, etc. Generally, the alcohol comprises 40 to 80% by weight of the aqueous alcohol medium. As the dissolved 2,3-epoxytetralin reacts and forms thioepoxytetralin, the thioepoxytetralin precipitates from the reaction medium.

The 2,3-thioepoxytetralin can be homopolymerized or copolymerized to polysulfides having a molecular weight of 10,000 to 25,000 or more by reacting the 2,3-thioepoxytetralin in a suitable solvent using a suitable polymerization catalyst. Suitable comonomers include ethylene oxide, ethylene episulfide, propylene oxide, propylene episulfide, 2,3-epoxytetralin, etc. For example, 2,3-thioepoxytetralin can be polymerized in a halohydrocarbon, such as methylene dichloride, 1,1,1-trichloroethane, etc. under nitrogen using either $BF_3$ etherate or stannic chloride.

Although poly(2,3-thioepoxytetralin) can be produced by polymerizing 2,3-thioepoxytetralin at 0° C. using stannic chloride catalyst, lower temperatures (about −70° C.) are required for the $BF_3$ etherate catalyst. At 0° C., using $BF_3$ etherate catalyst, bis-(1,4-dihydronaphtho) [2,3-c; 2,3-f] 1,2,5-trithiepane is produced.

The poly(2,3-thioepoxytetralin) and poly (2,3-epoxytetralin) of Rothrock U.S. Pat. No. 3,054,099 can be chain extended by reaction with diisocyanates, such as toluene diisocyanate, to increase the polymer molecular weight. The chain extended polymers or the base polymers can be used to form fibers or as adhesives.

The following examples are merely illustrative.

EXAMPLE I

Twenty and one-half grams 2,3-epoxytetralin, 100 ml ethanol, 19.4 grams potassium thiocyanate and 50 ml water were stirred for five days at room temperature in a 250 ml-Erlynmeyer flask equipped with a magnetic stirrer. The mixture was filtered, washed with water and a white solid collected. The filtrate was stirred at room temperature for six more days, filtered, washed with water and a white solid combined with the first crop of solids, which had a combined weight of 14.65 grams (65% yield). After recrystallization from ethyl ether, the 2,3-thioepoxytetralin melted at 73° C. The nmr, IR and analytical data were all consistent with 2,3-thioepoxytetralin.

|  | Theory | Found |
|---|---|---|
| Carbon | 74.03 | 74.28 |
| Hydrogen | 6.21 | 6.16 |

One and forty-three one-hundredths grams 2,3-thioepoxytetralin, 5 ml of methylene dichloride and 0.056 ml $BF_3$ etherate were placed in a vial under nitrogen and sealed. After standing at 0° C. for 24 hours, 0.8 grams of crystals were filtered off. The product was recrystallized from benzene and melted at 189°–190° C. Mass spectrum and chemical analysis indicated that the compound was bis-(1,4-dihydronaphtho) [2,3-c; 2,3-f] 1,2,5-trithiepane.

|  | Theory | Actual |
|---|---|---|
| Carbon | 67.37 | 68.01 |
| Hydrogen | 5.65 | 5.67 |
| Sulfur | 26.98 | 26.11 |

EXAMPLE III

One and forty-three one-hundredths grams 2,3-thioepoxytetralin, 5 ml of methylene dichloride and 0.28 ml $BF_3$ etherate were placed in a vial under nitrogen and sealed. After standing at −75° C. for 5 hours, the vial was opened and the reaction quenched with 1 ml methanol. The reaction mixture was allowed to equilibrate to room temperature, poured into excess methanol and the poly(2,3-thioepoxytetralin) recovered by filtration. The resinous polymer had a molecular weight of 15,000 and was obtained in 90% yields.

EXAMPLE IV

Example III was repeated using varying concentrations of stannic chloride catalyst in place of the $BF_3$ etherate and 0° C. reaction temperature. The results are set forth below in Table I.

Table I

| % moles Stannic Chloride based on thioepoxide | Molecular Weight of Polymer | % Yield |
|---|---|---|
| 0.01% | 1500 | 54 |
| 0.10% | 2000 | 62 |
| 0.50% | 6000 | 64 |
| 1.0% | 10000 | 78 |
| 5% | 16000 | 92 |

Table I-continued

| % moles Stannic Chloride based on thioepoxide | Molecular Weight of Polymer | % Yield |
|---|---|---|
| 10% | 25000 | 68 |
| 15% | 15000 | 25 |
| 25% | 8000 | 7 |

The data indicates highest yield is obtained using about 5% moles stannic chloride catalyst while highest molecular weight is obtained using about 10% moles stannic chloride catalyst.

I claim:
1. Bis-(1,4-dihydronaphtho)[2,3-c; 2,3-f] 1,2,5-trithiepane.